United States Patent
Schramm et al.

(10) Patent No.: US 8,465,763 B2
(45) Date of Patent: Jun. 18, 2013

(54) 3-HYDROXYCHLORMADINONE ACETATE FOR THE TOPICAL TREATMENT OF ANDROGEN-DEPENDENT SKIN DISEASES

(75) Inventors: Georg Schramm, Stolberg (DE); Christa Kneip, Aachen (DE)

(73) Assignee: Richter Gedeon Nyrt., Budapest (HU)

( * ) Notice: Subject to any disclaimer, the term of this patent is extended or adjusted under 35 U.S.C. 154(b) by 769 days.

(21) Appl. No.: 12/483,869

(22) Filed: Jun. 12, 2009

(65) Prior Publication Data

US 2009/0318395 A1 Dec. 24, 2009

Related U.S. Application Data

(63) Continuation of application No. PCT/EP2007/011144, filed on Dec. 19, 2007.

(30) Foreign Application Priority Data

Dec. 22, 2006 (DE) .......................... 10 2006 062 120

(51) Int. Cl.
*A61F 13/00* (2006.01)
*A61K 9/70* (2006.01)

(52) U.S. Cl.
USPC ........... 424/449; 514/859; 514/864; 514/880; 514/944; 514/945

(58) Field of Classification Search
USPC .................. 424/449; 514/859, 864, 880, 944, 514/945
See application file for complete search history.

(56) References Cited

U.S. PATENT DOCUMENTS

| 3,328,432 A | | 6/1967 | Bruckner et al. | |
| 5,587,176 A | * | 12/1996 | Warren et al. | 424/443 |
| 5,723,146 A | * | 3/1998 | Rossling et al. | 424/450 |

FOREIGN PATENT DOCUMENTS

| EP | 0765663 A2 | 4/1997 |
| WO | 86/01402 | 3/1986 |
| WO | 91/06284 | 5/1991 |
| WO | 2007/137797 A1 | 12/2007 |

OTHER PUBLICATIONS

English Language Abstract for EP 0765663, Apr. 2, 1997.
English Language Abstract for WO 86/01402, Mar. 13, 1986.
Honma S et al: "Identification and Anti-Androgenic Activity of the Metabolites of 17Alpha-Acetoxy-6-Chloropregna-4,6-Diene-3,20-Dione (Chlormadinone Acetate) in the Rat, Rabbit, Dog an Dman" Chemical and Pharmaceutical Bulletin, Pharmaceutical Society of Japan, Tokyo, JP, vol. 25, No. 8, Aug. 25, 1977, pp. 2019-2031.

* cited by examiner

*Primary Examiner* — Lezah Roberts
*Assistant Examiner* — Nannette Holloman
(74) *Attorney, Agent, or Firm* — Jason D. Voight

(57) ABSTRACT

The present invention relates to the use of 3β-hydroxychlormadinone acetate (17α-acetoxychloropregna-4,6-dien-3β-ol-20-one) and/or 3α-hydroxychlormadinone acetate (17α-acetoxychloropregna-4,6-dien-3α-ol-20-one) for producing a medicament for treating skin, preferably human skin by means of topical application, and to a pharmaceutical or cosmetic composition containing 3β-hydroxychlormadinone acetate and/or 3α-hydroxychlormadinone acetate.

25 Claims, 1 Drawing Sheet

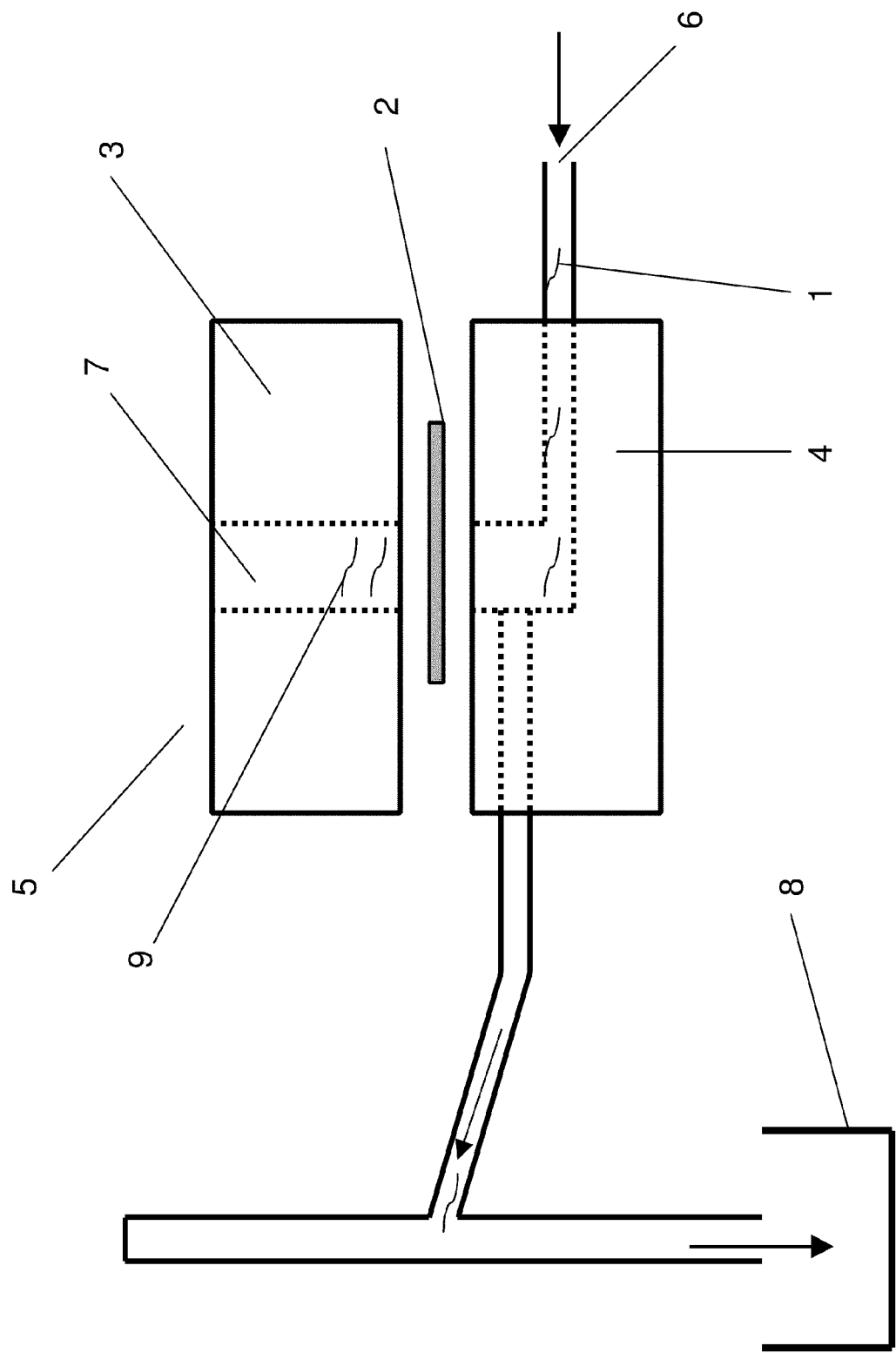

3-HYDROXYCHLORMADINONE ACETATE FOR THE TOPICAL TREATMENT OF ANDROGEN-DEPENDENT SKIN DISEASES

This application is a Continuation of 371 application of PCT/EP2007/011144 filed Dec. 19, 2007, which claims priority to the German application 10 2006 062 120.4 filed Dec. 22, 2006.

The present invention relates to the use of 3β-hydroxychlormadinone acetate (17α-acetoxychloropregna-4,6-dien-3α-ol-20-one) and/or 3α-hydroxychlormadinone acetate (17α-acetoxychloropregna-4,6-dien-3α-ol-20-one) for producing a medicament for treating skin, preferably human skin by means of topical application, and to a pharmaceutical or cosmetic composition containing 3β-hydroxychlormadinone acetate and/or 3α-hydroxychlormadinone acetate.

In Central Europe the proportion of skin conditions with hormonal causes, such as acne, alopecia, seborrhoea and/or hirsutism, is estimated at 35 or 50%. Acne, alopecia, seborrhoea and hirsutism are generally androgen-dependent diseases.

Acne, in particular "common" acne, mainly occurs as a result of elevated androgen levels during puberty. Alopecia is triggered inter alia by a genetically determined hypersensitivity to the hormone dihydrotestosterone (DHT), an androgenic hormone. Seborrhoea involves pathological changes in secretion from the sebaceous glands and in hirsutism women grow excessive amounts of body hair according to the male pattern.

Hormone treatment, in particular using gestagens with an antiandrogenic action, may have a favourable effect on the course of these androgen-dependent diseases. Such antiandrogenic gestagens are conventionally administered orally.

WO 86/01402, WO 91/06284 and EP 0 765 663 describe the gestagens chlormadinone acetate (CMA), cyproterone acetate (CPA) and megestrol acetate (MGA) respectively for producing a medicament for topical application in androgen-dependent diseases.

However, a disadvantage of these topically applied, antiandrogenically active medicaments is that the topical application thereof also leads at the same time to a high systemic load with the respective active ingredient.

The object of the present invention was therefore to provide a pharmaceutical or cosmetic composition for topical treatment and/or prevention of androgen-dependent diseases, the topical application of which causes a virtually negligible systemic load of the corresponding active ingredient. These compositions are therefore intended to be suitable for topical treatment of the skin and hair of both female and male patients.

This object is achieved by the use of 3β-hydroxychlormadinone acetate (17α-acetoxychloropregna-4,6-dien-3β-ol-20-one) and/or 3α-hydroxychlormadinone acetate (17α-acetoxychloropregna-4,6-dien-3α-ol-20-one) for producing a medicament for topical treatment of skin, preferably human skin, and optionally also hair.

The antiandrogenic active ingredients 3β-hydroxychlormadinone acetate and 3α-hydroxychlormadinone acetate are surprisingly distinguished by a far lesser degree of skin penetration compared with CMA, whereby a systemic active ingredient load is virtually prevented in the case of effective treatment of androgen-dependent diseases by topical application.

The present invention also provides a pharmaceutical composition for treating skin by topical application comprising 3β-hydroxychlormadinone acetate and/or 3α-hydroxychlormadinone acetate in a quantity of 0.01 to 20 wt. %, preferably 0.01 to 10 wt. %, relative to the total weight of the pharmaceutical composition according to the invention, and at least one pharmaceutically acceptable vehicle, preferably in conventional quantities.

For the purposes of the invention the term "pharmaceutically acceptable vehicle" means conventional pharmaceutical auxiliary substances and additives for the formulation of pharmaceutical compositions, such as pharmaceutically acceptable buffers, preservatives, reducing agents, antioxidants, UV absorbers, stabilisers, penetration promoters, emulsifiers, gelling agents, thickeners, surfactants, fragrances, aroma additives and colorants. Such auxiliary substances and additives are generally preferably pharmaceutically safe.

Suitable buffers which may be used for the pharmaceutical composition according to the invention are known to a person skilled in the art. Buffers which may accordingly be used are succinic acid, citric acid, lactic acid, phosphoric acid, trisodium phosphate, disodium hydrogenphosphate, sodium dihydrogenphosphate, sodium carbonate and combinations of lactic acid and sodium hydroxide. The pH value of the composition is preferably adjusted to 5.5-7.5 with the buffer.

Antioxidants, reducing agents and/or UV absorbers may be used as stabilisers or preservatives. For the pharmaceutical composition according to the invention, at least one reducing agent is particularly preferably selected from the group comprising sulfites, such as sodium sulfite, potassium sulfite, ammonium sulfite, sodium hydrogensulfite, potassium hydrogensulfite, sodium bisulfite, calcium sulfate, calcium hydrogensulfite, potassium bisulfite, sodium disulfite, ammonium hydrogensulfite, sodium metabisulfite, potassium metabisulfite; mercaptocarboxylic acids, such as 2-mercaptopropionic acid, 3-mercaptopropionic acid, mercaptosuccinic acid, thioglycolic acid, ammonium thioglycolate, sodium thioglycolate, L-cysteine, dimercaptoadipic acid; mercaptoamines, such as L-cysteine ethyl ester, L-cysteine methyl ester, N-acetyl-L-cysteine, cysteamine; mercaptoamides, such as thioglycolamide, N-hydroxyethylmercaptoacetamide, N-methylmercaptoacetamide, 2-mercaptopropionamide; hydroxides, such as guanidine hydroxide, sodium hydroxide; alcohols and diols, such as resorcinol, thioglycerol, glycerol monothioglycolate, glycol thioglycolate; dithio compounds, such as dihydrolipoic acid, sodium dihydrolipoic acid, dithiothreitol, 1,3-dithiopropanol; lithium chloride, tris(hydroxymethyl)phosphine, thioglycol hydrazide, 2-mercaptoethanesulfonic acid, homocysteinethiolactone, polythiol polymers, salts of hydrogen sulfide, amines in alkaline solution, salts of hydrogen cyanide, borohydride, dithionite, ester salts of sulfoxylates, formic acid, oxalic acid, diazolidinyl urea, iodopropynyl butyl carbamate, chloromethylisothiazolinone, methylisothiazolinone, butylparaben, ethylparaben, methylparaben, propylparaben, isobutylparaben and phenoxyethanol. The stabilisers are preferably used in a quantity of 0.001 to 2 wt. %, relative to the total weight of the pharmaceutical composition according to the invention.

The antioxidant component used for the pharmaceutical composition according to the invention is preferably at least one antioxidant selected from the group comprising ascorbic acid (vitamin C), sodium L-ascorbate, calcium L-ascorbate, ascorbyl palmitate, butylhydroxyanisole, butylhydroxytoluene, calcium disodium EDTA, propyl gallate, octyl gallate, dodecyl gallate (lauryl gallate), isoascorbic acid, sodium isoascorbate, lecithin, lactic acid, polyphosphate, sulfur dioxide, selenium, tocopherol (vitamin E), α-tocopherol, γ-tocopherol, δ-tocopherol, tin(II) chloride, citric acid, sodium citrate and potassium citrate. The antioxidant is preferably used in a quantity of 0.001 to 2 wt. %, relative to the total weight of the pharmaceutical composition according to the invention.

The following compounds may preferably be used as UV absorbers for the pharmaceutical composition according to the invention:

(A) p-Aminobenzoic acid (PABA) type UV absorbers, such as p-aminobenzoic acid, PABA monoglycerol ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA amyl ester and N,N-dimethyl PABA octyl ester.

(B) Anthranilic acid type UV absorbers, such as homomethyl-N-acetylanthranilic acid.

(C) Salicylic acid type UV absorbers: amyl salicylic acid, menthyl salicylic acid, homomethyl salicylic acid, octyl salicylic acid, phenyl salicylic acid, benzyl salicylic acid and/or p-isopropanol phenyl salicylic acid.

(D) Cinnamic acid type UV absorbers, such as octylcinnamic acid, ethyl-4-isopropylcinnamic acid, methyl-2,5-diisopropylcinnamic acid, ethyl-2,4-diisopropylcinnamic acid, methyl-2,4-diisopropylcinnamic acid, propyl-p-methoxycinnamic acid, isopropyl-p-methoxycinnamic acid, isoamyl-p-methoxycinnamic acid, octyl-p-methoxycinnamic acid (or 2-ethylhexyl-p-methoxycinnamic acid), 2-ethoxyethyl-p-methoxycinnamic acid, cyclohexyl-p-methoxycinnamic acid, ethyl-α-cyano-β-phenylcinnamic acid, 2-ethylhexyl-α-cyano-β-phenylcinnamic acid and/or glycerol mono-2-ethylhexanoyl diparamethoxycinnamic acid.

(E) Benzophenone type UV absorbers, such as 2,4-dihydroxybenzophenone, 2,2'-dihydroxy-4-methoxybenzophenone, 2,2'-dihydroxy-4,4'-dimethoxy-benzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonic acid salts, 4-phenylbenzo-phenone, 2-ethylhexyl-4'-phenylbenzophenone 2-carboxylate, 2-hydroxy-4-n-octoxybenzophenone and/or 4-hydroxy-3-carboxybenzophenone.

(F) Other UV absorbers, such as 3-(4'-methylbenzylidene)-D,L-camphor, 3-benzylidene-D,L-camphor, urocanic acid, ethyl urocanic acid, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methylphenyl)benzotriazole, dibenzalazine, dianisoylmethane, 4-methoxy-4'-t-butyldibenzoylmethane, 5-(3,3-dimethyl-2-norbornylidene)-3-pentan-2-one, calcium lakes, barium oxide, aluminium oxide, iron oxide and/or titanium dioxide.

The UV absorber is preferably used in a quantity of 1 to 10 wt. %, relative to the total weight of the pharmaceutical composition according to the invention.

The pharmaceutical composition according to the invention may optionally contain further, pharmaceutically acceptable additives, such as for example penetration promoters, solvents such as water and/or alcohols, surface-active substances, gelling agents, softeners, emulsifiers, stabilisers, hydrophobic or hydrophilic polymers, fragrances, film formers and/or thickeners, insofar as such additives do not influence skin penetration.

Penetration promoters suitable for the purposes of the present invention preferably comprise penetration promoters selected from the group comprising acid amides and amines. Urea is particularly preferred as a penetration promoter. The penetration promoter is preferably used in a quantity of 0.5 to 10 wt. %, relative to the total weight of the pharmaceutical composition according to the invention.

Emollients may be used in formulating the pharmaceutical composition according to the invention in quantities such that drying-out of the skin is prevented or reduced. The emollient may preferably take the form of at least one compound selected from the group comprising oils, waxes, silicone oils, triglyceride esters, acetoglyceride esters, ethoxylated glycerides, alkyl esters, alkenyl esters, fatty acids, fatty alcohols, fatty alcohol esters, lanolin, lanolin derivatives, polyhydrogenated alcohols, the ethers thereof, polyhydrogenated alcohol esters, wax esters, beeswax derivatives, vegetable waxes, phospholipids, sterols and amides. The emollients are preferably used in a quantity of 1 to 25 wt. %, relative to the total weight of the composition according to the invention.

Preferred emulsion stabilisers in the composition according to the invention comprise nonionic, anionic, cationic and amphiphilic surfactants, which are preferably selected from the group comprising polyethylene glycol derivatives, polyethylene glycerol derivatives, Tweens, Tritons, Spans, polyglycerols, polyalkyl glycerides, alkyl sulfonates, aryl sulfonates, alkyl phosphates, aryl phosphates, alkyl betaine derivatives and phosphatidyl glycerol. The emulsion stabilisers are preferably used in a quantity of 0.1 to 5 wt. %, relative to the total weight of the composition according to the invention.

Emulsifiers are preferably added to the composition in quantities such that they enable uniform mixing of the components of the pharmaceutical composition according to the invention. Conventional emulsifiers are preferably anionic, cationic and/or nonionic emulsifiers. Examples of such emulsifiers preferably comprise potassium stearate, sodium stearate, ammonium stearate, triethanolamine stearate, glycerol monostearate, sodium lauryl 5-sulfate, sodium acetyl sulfate, N-(stearoylcolaminoformylmethyl)-pyridinium chloride, N-soya-N-ethylmorpholine ethosulfate, alkyl dimethylbenzylammonium chloride, diisobutyl phenoxythioxy ethyldimethylbenzylammonium chloride, acetylpyridinium chloride, monostearate, polyethylene oxide stearate, polyethylene oxide sorbitan monostearate, sorbitan, propylene glycol monostearate and/or ethoxylated lanolin. The emulsifier component is preferably used in a quantity of 0.1 to 10 wt. %, relative to the total weight of the pharmaceutical composition according to the invention.

Furthermore, surface-active substances (surfactants), which have nonionic, cationic, anionic and/or ampholytic properties, may also be used.

Nonionic surface-active substances are preferably used for producing the pharmaceutical composition according to the invention, these preferably comprising sorbitan esters, such as sorbitan monolaurate, sorbitan monooleate, sorbitan monoisostearate; polyethylene oxide sorbitan esters, such as polyethylene oxide sorbitan monoisostearate, polyethylene oxide sorbitan monolaurate, polyethylene oxide sorbitan monooleate; glycerol esters, such as glycerol monoisostearate, glycerol monomyristate; polyethylene oxide glycerol ethers, such as polyethylene oxide glycerol monoisostearate, polyethylene oxide glycerol monomyristate; polyglycerol fatty acid esters, such as diglycerol monostearate, decaglycerol decaisostearate, diglycerol diisostearate; glycerol fatty acid esters, such as glycerol monocaprate, glycerol monolaurate, glycerol monomyristate, glycerol monopalmitate, glycerol monooleate, glycerol monostearate, glycerol monolinoleate, glycerol monoisostearate, glycerol monodilinoleate, glycerol monodicaprate; polyethylene oxide glycerol fatty acid esters, such as polyethylene oxide glycerol monomyristate, polyethylene oxide glycerol monooleate, polyethylene oxide glycerol monostearate; polyethylene oxide-branched alkyl ethers, such as polyethylene oxide octyldodecyl alcohol, polyethylene oxide-2-decyl tetradecyl alcohol; polyethylene oxide alkyl ethers, such as polyethylene oxide oleyl alcohol ether, polyethylene oxide acetyl alcohol ether; polyethylene oxide-hydrogenated castor oil fatty acid esters, such as polyethylene oxide-hydrogenated castor oil, polyethylene oxide dihydrocholesterol ether, polyethylene oxide-hydrogenated castor oil isostearate and/or polyethylene oxide alkyl aryl ether, such as polyethylene oxide octyl phenol ether.

Anionic surface-active substances used for the pharmaceutical composition according to the invention preferably comprise salts, such as diethanolamine salt, triethanolamine salt, amino acid salt, sodium salt, potassium salt; higher fatty acids, such as oleic acid, stearic acid, isostearic acid, palmitic acid, myristic acid, ether carboxylic acid alkaline salts, N-acyl amino acid salts and higher alkylsulfonic acid salts. The surface-active substance is preferably used in a quantity of 0.1 to 10 wt. %, relative to the total weight of the pharmaceutical composition according to the invention.

Gel formers suitable for the compositions according to the invention preferably comprise natural or synthetic polymers. Natural polymers are preferably selected from the group comprising agar-agar, alginic acid, alginate, amidated pectin, propylene glycol alginate, carbomer, carrageenan, casein, dammar gum, dextrins, furcellaran, gelatin, guar gum, guar flour, gellan, gum ghatti, gum arabic, spruce sap gum, locust bean flour, karaya gum, keratin, konjac flour, L-HPC, locust bean gum, mastic, pectin, shellac, (optionally modified) starch, tara stone flour, tragacanth, xanthan gum and the derivatives thereof. Preferred synthetic polymers which may be used as gelling agents for the composition according to the invention are selected from the group comprising acrylic acid polymers, carbomers, polyacrylamides and alkylene oxide polymers. The gel formers are preferably used in a quantity of 0.1 to 5 wt. %, relative to the total weight of the composition according to the invention.

Thickeners which may preferably be present in the compositions according to the invention comprise, for example, candelilla, carnauba and microcrystalline waxes, carbomers and polyethylene oxide thickeners. The thickener is preferably used in a quantity of 0.5 to 2 wt. %, relative to the total weight of the pharmaceutical composition according to the invention.

The pharmaceutical composition according to the invention may preferably contain at least one colorant and/or one fragrance.

In a preferred embodiment of the pharmaceutical composition according to the invention, a fragrance or aroma additive is present in the form of at least one compound selected from the group comprising unsaturated or saturated, acyclic, monocyclic or bicyclic monoterpenes and sesquiterpenes, which may in each case be substituted with 1, 2, 3 or 4 identical or different substituents selected from the group comprising an —OH, oxo (═O or —O—), —O—$C_{1-5}$-alkyl, —O-phenyl, —C(═O)—OH, —C(═O)—O—$C_{1-5}$-alkyl, —C(═O)—O-phenyl, —O—C(═O)—$C_{1-5}$-alkyl, —O—C(═O)-phenyl group and —CN, the alkyl and/or phenyl residue possibly being substituted with 1, 2 or 3 substituents selected from the group comprising OH, oxo (═O) and —O—$C_{1-5}$-alkyl;

phenyl or naphthyl compounds, which may in each case be substituted with 1, 2, 3, 4 or 5 identical or different substituents selected from the group comprising a —C(═O)—H, —C(═O)—$C_{1-5}$-alkyl, —C(═O)-phenyl, —OH, —$C_{1-5}$ alkyl, —$C_{2-5}$ alkenyl, —O—$C_{1-5}$-alkyl, —O—C(═O)—$C_{1-5}$-alkyl, —O—C(═O)—$C_{2-6}$-alkylene, —O—C(═O)-phenyl, —O—C(═O)—OH, phenyl, —C(═O)—OH, —C(═O)—O—$C_{1-5}$-alkyl, —C(═O)—O—$C_{2-8}$-alkenyl, —C(═O)—O-phenyl, —C(═O)—O—$C_{3-8}$-cycloalkyl, —CH═C(—$C_{1-5}$-alkyl)(C(═O)—H), —$NO_2$ and —$NH_2$ group, the substituents in each case possibly being attached by way of a linear or branched $C_{1-7}$ alkylene or $C_{2-5}$ alkenylene bridge, which may in each case be substituted with 1, 2 or 3 identical or different substituents selected from the group comprising F, Cl, and Br;

phenyl or naphthyl compounds, which may be condensed with 1 or 2 unsaturated or saturated 5- to 7-membered aliphatic rings, wherein the rings may in each case comprise 1, 2 or 3 heteroatom(s) selected from the group consisting of oxygen, nitrogen and sulfur as ring member(s) and be substituted with 1, 2, 3, 4 or 5 identical or different substituents selected from the group comprising a —$C_{1-5}$ alkyl, —OH and —O—$C_{1-5}$-alkyl group;

and unsaturated or saturated, unsubstituted, linear, branched or cyclic esters, alcohols and aldehydes, which comprise 5 to 20, preferably 5 to 16, carbon atoms and optionally 1, 2 or 3 heteroatom(s) selected from the group consisting of oxygen and sulfur as chain link(s) or ring member(s).

The pharmaceutical composition according to the invention particularly preferably contains as fragrance or aroma additive at least one natural or nature-identical compound selected from the group comprising anethole, benzaldehyde, benzyl acetate, benzyl alcohol, benzyl formate, iso-bornyl acetate, camphor, neral, citronellal, citronellol, citronellyl acetate, para-cymene, decanal, dihydrolinalool, dihydromyrcenol, dimethylphenylcarbinol, eucalyptol, geraniol, geranyl acetate, geranyl nitrile, cis-3-hexenyl acetate, hydroxycitronellal, limonene, linalool, linalool oxide, linalyl acetate, linalyl propionate, methyl anthranilate, alpha-methylionone, methylnonylacetaldehyde, methylphenylcarbinyl acetate, menthone, iso-menthone, myrcene, myrcenyl acetate, myrcenol, nerol, neryl acetate, nonyl acetate, phenylethyl alcohol, alpha-pinene, beta-pinene, gamma-terpinene, alpha-terpinol, beta-terpinol, terpinyl acetate, para-tert.-butylcyclohexyl acetate, alpha-amylcinnamaldehyde, amyl salicylate, caryophyllene, cedrene, cinnamyl alcohol, dimethylbenzylcarbinyl acetate, ethylvanillin, eugenol, iso-eugenol, tricyclodecenyl acetate, piperonal, 3-cis-hexenyl salicylate, hexyl salicylate, lilial, gamma-methylionone, nerolidol, patchouli alcohol, phenylhexanol, beta-selinene, trichlormethylphenylcarbinyl acetate, triethyl citrate, vanillin, dimethoxybenzaldehyde, benzophenone, ethylene brassylate, galaxolide, hexylcinnamaldehyde, lyral, methyl cedryl ketone, methyl beta-naphthyl ketone, musk ketone, phenylethyl phenyl acetate, ambrettolide, cyclohexyl salicylate, delta-nonalactone, delta-undecalactone, dodecalactone, ethyl undecylenate, exaltolide, gamma-undecalactone, hexadecanolide, myristicin and musk xylene.

Further fragrances or aroma additives which may be present in the pharmaceutical composition according to the invention are disclosed in David J. Rowe, Chemistry and Technology of Flavors and Fragrances, Taylor & Francis Group, 2004; Michael Edwards, Fragrances of the World 2005, Crescent House Pub., 2004 and David Pybus, The Chemistry of Fragrances, Royal Society of Chemistry, 1999. The corresponding disclosures are hereby deemed to be part of the present disclosure.

At least one naturally occurring mixture of fragrances or aroma additives may also be used as a fragrance for the pharmaceutical composition according to the invention. In particular, at least one suitable fragrance or aroma additive mixture is selected from the group comprising rosemary oil, sandalwood oil, violet oil, lemon grass oil, lavender flower oil, eucalyptus oil, peppermint oil, chamomile oil, clove leaf oil, cinnamon oil, thyme oil, tea tree oil, cajeput oil, niaouli oil, manuka oil, citrus oil, mountain pine oil, jasmine oil, geranium oil, caraway oil, pine-needle oil, bergamot oil, terpentine oil, linalol oil, blood orange oil, cypress oil, silver fir oil, fennel oil, grapefruit oil, ginger oil, pine-needle oil, lavandin oil, lemon-grass oil, lime oil, mandarin oil, melissa oil, myrrh oil, patchouli oil, rosewood oil and thuja oil. The fragrance or aroma additive is preferably used in a quantity of 0.001 to 2 wt. %, relative to the total weight of the pharmaceutical composition according to the invention.

Colorants which are preferably used for the pharmaceutical composition according to the invention comprise:
 A) inorganic and organic pigments, such as for example titanium dioxide, zirconium oxide, cerium oxide, zinc oxide, iron oxide, Prussian blue, carbon blacks calcium lakes and aluminium lakes.
 B) fat-soluble dyes, such as for example Sudan Red, DC Red 17, DC Green 6, beta-carotene, soy oil, Sudan Brown, DC Yellow 11, DC Violet 2, DC Orange 5 and Quinoline Yellow.
 C) water-soluble colorants, such as for example iron sulfates, (rhodamines), methylene blue and natural colorants.

The colorant is preferably used in a quantity of 0.001 to 2 wt. %, relative to the total weight of the pharmaceutical composition according to the invention.

The pharmaceutical composition according to the invention is preferably distinguished in that the active ingredient(s) 3β-hydroxychlormadinone acetate and/or 3α-hydroxychlormadinone acetate is/are preferably distributed in molecularly disperse manner in a hydrophilic component.

The hydrophilic component used preferably comprises sugar or sugar-like substances, such as sucrose, lactose, mannitol, sugar alcohol, urea or other nitrogenous compounds.

Alternatively, the pharmaceutical composition according to the invention may preferably contain the active ingredient 3β-hydroxychlormadinone acetate and/or 3α-hydroxychlormadinone acetate distributed in molecularly disperse manner in a moisturising base, optionally in combination with a hydrophilic component.

Such a preparation based on a moisturising base additionally counteracts stimulation of the skin to overproduce grease, in that a certain quantity of grease, necessary for reconstitution of the skin, is made available in a controlled manner. Conventional moisturising preparations are known to a person skilled in the art and comprise for example lipogels or oil-in-water emulsions.

The pharmaceutical composition according to the invention may be formulated as a liquid, foam, cream, gel, paste, balsam, spray, ointment, lotion, rinse (conditioner), tonic, tincture, milk, purée, powder for dissolution, emulsion (oil-in-water, water-in-oil), serum, oil, shampoo, suspension such as liposomes or nanosomes, or as a dispersion.

The production of corresponding formulations containing the pharmaceutical composition according to the invention and the auxiliary substances and additives conventionally used therein are known to a person skilled in the art. In this respect, reference is made for example to Bauer et al., "Lehrbuch der pharmazeutischen Technologie" 6th edition, WVG Stuttgart, 1999, the relevant disclosures thereof being hereby introduced as part of the disclosure of the present application.

The pharmaceutical composition according to the invention is particularly preferably distinguished in that it contains as vehicle at least one buffer, at least one preservative, at least one aroma additive and/or at least one auxiliary substance and is preferably formulated as a cream, ointment, lotion, gel, tincture, mask suitable for application, spreadable composition, facial lotion, hair balsam, hair conditioner, hair gel, hair tonic, hair lotion, hair cream or hair shampoo.

The present invention further provides a cosmetic composition for care of the skin and optionally also the hair by topical or external application comprising 0.01 to 5 wt. %, preferably 0.01 to 2 wt. %, of 3β-hydroxychlormadinone acetate and/or 3α-hydroxychlormadinone acetate and at least one cosmetic vehicle, preferably in conventional quantities, the percentage content of 3β-hydroxychlormadinone acetate and/or 3α-hydroxychlormadinone acetate in each case being related to the total weight of the cosmetic composition according to the invention.

The conventional auxiliary substances and/or additives for cosmetic compositions are preferably suitable as cosmetic vehicles. Preferably, the above-listed auxiliary substances and additives may be used which are used for the formulation of pharmaceutical compositions. These additives or auxiliary substances are likewise preferably physiologically acceptable. The quantities of the particular components are preferably selected such that the cosmetic composition according to the invention complies with EU Cosmetics Directive 76/768/EEC or EU Directive 95/17/EC.

As already stated, it has surprisingly been found that the antiandrogenic active ingredients 3β-hydroxychlormadinone acetate and 3α-hydroxychlormadinone acetate are distinguished by 6-times lower skin penetration and a 0.7-times greater antiandrogenic efficacy compared with CMA. As a result of these advantageous properties, systemic active ingredient load is virtually prevented in the case of topical treatment of androgen-dependent diseases.

The present invention accordingly also provides the use of 3β-hydroxychlormadinone acetate and/or 3α-hydroxychlormadinone acetate for producing a medicament for topical treatment of skin, preferably human skin and optionally hair, preferably for local topical treatment of androgen-dependent diseases, very particularly preferably for the prevention and/or treatment of androgen-dependent diseases such as acne, alopecia, seborrhoea and/or hirsutism.

Acne is principally a disease of the sebaceous gland follicle, which initially causes non-inflammatory comedones but may subsequently also cause the occurrence of a range of inflammatory efflorescences (inter alia papules, pustules and nodules). In some forms of acne, terminal and vellus hair follicles may be affected.

Acne is classified depending on cause, form or severity and age.

Acne may however also have an exogenous (external) cause.

Acne inversa is a frequently severe inflammation of the sebaceous glands and terminal hair follicles, preferably in intertriginous areas such as for example the armpits, groin region and gluteal fold.

Depending on form or severity, a distinction is drawn between acne comedonica, acne papulopustulosa and acne conglobata. In acne comedonica, the skin displays comedones and at most a few, very slight instances of inflammation (papules). Scarring need not be feared. In acne papulopustulosa, papules and pustules dominate, scarring is possible as a consequence of the inflammatory processes. Acne conglobata denotes the additional occurrence of fistular comedones and nodules, with considerable scarring as the probable consequence. Acne may occur in both acute and chronic form.

Alopecia very generally denotes visible loss of hair from the scalp, i.e. it is a condition distinguished by abnormally "thin" hair on the head or by hairless areas of the skin resulting in baldness.

The most frequently occurring form of alopecia comprises androgenetic hair loss (alopecia androgenetica).

Seborrhoea is a medical term for pathologically changed sebaceous gland secretion. It is associated with a deficiency of biotin (vitamin B7) and vitamin B6 (pyridoxine). The term is sometimes also used for seborrhoeic eczema. Patients with seborrhoea often also suffer from dry skin and keratinisation. Seborrhoea oleosa makes the skin oily, while seborrhoea sicca manifests itself in bran-like, greasy flakes. Seborrhoea encourages inter alia the occurrence of rosacea, acne vulgaris and acne necroticans.

According to the International Statistical Classification of Diseases and Related Health Problems (ICD—International Classification of Diseases) of the World Health Organization (WHO), seborrhoea is assigned to the categories "seborrhoeic dermatitis" L21 and "seborrhoeic keratosis" L82, class L21 being further subdivided into the subclasses L21.0 (seborrhoea capitis, cradle cap), L21.1 (seborrhoeic infantile dermatitis), L21.8 (other seborrhoeic dermatitis), L21.9 (seborrhoeic dermatitis, unspecified) and class L82 comprising the diseases dermatosis papulosa nigra and Leser-Trélat disease.

Hirsutism (ICD class L68.0) is excessive hair growth in women according to the male pattern, which may be triggered either by increased formation of male sex hormones (testosterone) or by psychogenic factors such as social stress or an anxiety syndrome.

Particular preference is given to the use of 3β-hydroxychlormadinone acetate and/or 3α-hydroxychlormadinone acetate for producing a medicament for prevention and/or treatment of seborrhoea, acne, alopecia, and/or hirsutism, such prevention and/or treatment preferably comprising local, topical treatment of the skin and/or hair and/or for promoting hair growth in both female and male patients. Preferably local, topical application of the medicament for treating seborrhoea, acne vulgaris, androgenetic alopecia, and/or hirsutism is particularly preferred.

The medicament according to the invention preferably contains 0.01 to 20, more preferably 0.01 to 10 and very particularly preferably 0.01 to 5 wt. % of 3β-hydroxychlormadinone acetate and/or 3α-hydroxychlormadinone acetate, relative in each case to the total weight of the medicament according to the invention.

The present invention also provides the use of a cosmetic composition, as described above, for care of the skin and optionally also the hair, preferably in humans, by topical application, preferably for the prevention of and/or application in the case of seborrhoea and/or acne, preferably acne vulgaris, androgenetic alopecia and/or for promoting hair growth in both female and male patients.

For topical treatment, the pharmaceutical or cosmetic composition according to the invention is preferably applied at least once daily, particularly preferably 3 times daily and very particularly preferably twice daily to the human skin and/or to the hair.

Preferably, the pharmaceutical or cosmetic composition according to the invention is applied to the scalp, facial skin, the skin of the upper body, such as for example the skin of the back and/or the chest and/or to the hair.

The following examples serve to explain the invention further but should not to be construed as limiting the scope thereof:

EXAMPLE 1

A pharmaceutically active solution of:

| | |
|---|---|
| 3β-Hydroxychlormadinone acetate | 2.0 g |
| Isopropyl myristate | 10 g |
| EDTA (ethylenediaminetetraacetic acid) | 0.025 g |
| Ethanol, 96% | 35.0 g |
| Transcutol (diethylene glycol monoethyl ether) | 2.0 g |
| Propylene glycol | 50.975 g | is produced by mixing and dissolving the components.

EXAMPLE 2

A cosmetic solution of:

| | |
|---|---|
| 3β-Hydroxychlormadinone acetate | 1.0 g |
| Carbomer 940 | 1.0 g |
| Propylene glycol | 10.0 g |
| Na-EDTA | 0.025 g |
| Methyl parabens | 0.12 g |
| Propyl parabens | 0.05 g |
| Urea | 2.0 g |
| Purified water | 75.8 g | is produced by mixing and dissolving the components and subsequently adjusting the pH value to 5.5 using a 10% NaOH solution.

EXAMPLE 3

Determination of Permeation of Chlormadinone Acetate (CMA) and 3β-Hydroxychlormadinone Acetate Through Human Abdominal Skin Fragments of human abdominal skin arising during stomach reduction operations were placed in a Petri dish with dissection solution (Na$^+$: 144 mmol/l, K$^+$: 5.9 mmol/l, Ca$^{2+}$: 3.7 mmol/l, Cl,$^-$: 157 mmol/l). The skin fragments were reduced in thickness from the corium side, in several steps, down to a layer thickness of approx. 300 μm, while being kept moist with the dissection solution. Mechanically stable dissected skin was thus obtained, consisting of epidermis with approx. 150-200 μm of cutis. The layer thickness of the dissected skin fragments was determined by measuring with an external screw-type micrometer made by MITUTOYO. The area of the dissected skin fragments used amounted to approx. 19.7 mm$^2$.

Permeation of CMA respectively 3β-hydroxychlormadinone acetate through human abdominal skin was determined in a flow-through cell, which is illustrated schematically in FIG. 1. A receptor fluid (1) was here pumped past the underside of the dissected skin (2) with a peristaltic pump at a rate of 270 μl per hour. The dissected skin was clamped between the upper part (3) and the lower part (4) of the permeability cell (5). From above, vehicle with 3β-hydroxychlormadinone acetate (5% suspension in aqueous 0.05% polysorbate 80 solution) or chlormadinone acetate (5% suspension in aqueous 0.05% polysorbate 80 solution) was applied in each case to the skin, which then diffused through the dissected skin (2) into the receptor fluid (1). The dissected skin was moistened by a stationary donor fluid (9), which is situated in a reservoir (7). The internal diameter of the receptor fluid feed line (6) was 0.6 mm, and the receptor fluid volume below the skin amounted to approx. 80 µl. The receptor fluid (1) was analysed at fixed intervals by means of a fraction collector (8) and then by HPLC. These experiments allowed a quantitative statement to be made about the amount of substance diffused as a function of time.

An aqueous, isotonic tris buffer (20 mmol/l) with 20% ethanol was used as the receptor fluid and adjusted with NaCl to 310 mosmol (0.9 wt. %). The pH value of the receptor fluid was 7.35. A hole punch was used to punch a piece corresponding to the area of the dissected skin out of a plaster containing the active ingredient to be investigated, said piece being stuck to the dissected skin. The duration of the test was 21 h and the sampling interval was 3 h. The experiments were carried out at a test temperature of 34° C. In each case 3 independent series of measurements were made with CMA respectively 3β-hydroxychlormadinone acetate.

The average dose released (mean of 3 independently performed experiments) by human abdominal skin after 24 hours was in each case 4.4 µg for CMA and 0.7 µg for the metabolite 3β-hydroxychlormadinone acetate. The skin permeability of 3β-hydroxychlormadinone acetate is thus far less than that of CMA.

LIST OF REFERENCE NUMERALS

1 Receptor fluid (mobile phase)
2 Dissected skin
3 Upper part of the permeability cell
4 Lower part of the permeability cell
5 Permeability cell
6 Receptor fluid feed line
7 Reservoir for donor fluid
8 Fraction collector
9 Donor fluid (stationary phase)

The invention claimed is:

1. A pharmaceutical composition for treating the skin by means of topical application, comprising 0.01 to 20 wt. % of 3β-hydroxychlormadinone acetate (17α-acetoxychloropregna-4,6-dien-3β-ol-20-one) or 3α-hydroxychlormadinone acetate (17α-acetoxychloropregna-4,6-dien-3α-ol-20-one), or mixtures thereof and at least one pharmaceutically acceptable vehicle wherein the composition is formulated as a cream, ointment, lotion, gel, tincture, mask, facial lotion, hair balsam, hair conditioner, hair gel, hair tonic, hair lotion, hair cream or hair shampoo.

2. A cosmetic composition for care of the skin by topical application comprising 0.01 to 5 wt. % of 3β-hydroxychlormadinone acetate or 3α-hydroxychlormadinone acetate or mixtures thereof and at least one cosmetic vehicle wherein the composition is formulated as a cream, ointment, lotion, gel, tincture, mask, facial lotion, hair balsam, hair conditioner, hair gel, hair tonic, hair lotion, hair cream or hair shampoo.

3. A pharmaceutical composition according to claim 1 comprising at least one buffer, at least one preservative, at least one aroma additive or at least one auxiliary substance.

4. A pharmaceutical composition according to claim 3, wherein the preservative is at least one compound selected from the group consisting of antioxidants, reducing agents and UV absorbers.

5. A pharmaceutical composition according to claim 3, wherein characterised the 3β-hydroxychlormadinone acetate or 3α-hydroxychlormadinone acetate is distributed in molecularly disperse manner in a hydrophilic component.

6. A pharmaceutical composition according to claim 3, wherein the active ingredient 3β-hydroxychlormadinone acetate or 3α-hydroxychlormadinone acetate is distributed in molecularly disperse manner in a moisturising base.

7. A pharmaceutical composition according to claim 3, wherein the composition contains a penetration promoter.

8. A pharmaceutical composition according to claim 3, wherein the composition contains at least one colorant or one fragrance.

9. A pharmaceutical composition according to claim 3, suitable for at least once daily topical treatment of human skin.

10. A cosmetic composition according to claim 2, suitable for at least once daily care of human skin.

11. A pharmaceutical composition according to claim 6, wherein the 3β-hydroxychlormadinone acetate or 3α-hydroxychlormadinone acetate is distributed in molecularly disperse manner in a moisturizing base in combination with a hydrophilic component.

12. A pharmaceutical composition according to claim 7, wherein the penetration promoter is a compound selected from the group consisting of acid amides and amines.

13. A pharmaceutical composition according to claim 9, wherein the composition is applied to the scalp, facial skin, skin of the upper body, skin of the back, skin of the chest or hair.

14. A cosmetic composition according to claim 2, comprising at least one buffer, at least one preservative, at least one aroma additive or at least one auxiliary substance.

15. A cosmetic composition according to claim 14, wherein the preservative is at least one compound selected from the group consisting of antioxidants, reducing agents and UV absorbers.

16. A cosmetic composition according to claim 14, wherein the 3β-hydroxychlormadinone acetate or 3α-hydroxychlormadinone acetate is distributed in molecularly disperse manner in a hydrophilic component.

17. A cosmetic composition according to claim 14, wherein 3β-hydroxychlormadinone acetate or 3α-hydroxychlormadinone acetate is distributed in molecularly disperse manner in a moisturizing base.

18. A cosmetic composition according to claim 14, wherein the composition contains a penetration promoter.

19. A cosmetic composition according to claim 14, wherein the composition contains at least one colorant or one fragrance.

20. A pharmaceutical composition according to claim 1 wherein the composition is used for the topical treatment of an androgen-dependent disease.

21. A pharmaceutical composition according to claim 20 wherein the androgen-dependent diseases are selected from acne, seborrhea, hirsuitism, and alopecia.

22. A pharmaceutical composition according to claim 1 wherein the composition is used for the promotion of hair growth in both female and male patients.

23. A method for treating androgen-dependent diseases comprising topically applying the composition according to claim 1 to a patient in need thereof.

24. A method according to claim 23 wherein the androgen-dependent diseases are selected from acne, seborrhea, hirsuitism, and alopecia.

25. A method for promoting hair growth in a male or female comprising topically applying the composition according to claim 1 to a patient in need thereof.

* * * * *